(12) United States Patent
Lin et al.

(10) Patent No.: US 7,538,188 B2
(45) Date of Patent: *May 26, 2009

(54) METHOD FOR FABRICATING AN OLFACTORY RECEPTOR-BASED BIOSENSOR

(75) Inventors: Yuh-Jiuan Lin, Taipei Hsien (TW); Yuh-Fan Liu, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 10/962,722

(22) Filed: Oct. 12, 2004

(65) Prior Publication Data

US 2005/0074817 A1    Apr. 7, 2005

Related U.S. Application Data

(63) Continuation-in-part of application No. 10/262,832, filed on Oct. 3, 2002, now Pat. No. 7,186,799, and a continuation-in-part of application No. 09/535,814, filed on Mar. 28, 2000, now abandoned, which is a continuation-in-part of application No. 09/057,181, filed on Apr. 8, 1998, now abandoned.

(30) Foreign Application Priority Data

Dec. 21, 2001    (TW) .............................. 90131930 A (51) Int. Cl.
*A61K 38/08*    (2006.01)
*C12M 1/34*    (2006.01)
*G01N 33/00*    (2006.01)

(52) U.S. Cl. .................... 530/329; 435/287.9; 436/111; 436/112; 436/113

(58) Field of Classification Search ........................ None
See application file for complete search history.

(56) References Cited

U.S. PATENT DOCUMENTS

| | | | | |
|---|---|---|---|---|
| 5,541,289 | A | * | 7/1996 | Gilbertson .................. 530/327 |
| 5,932,432 | A | * | 8/1999 | Crowell et al. ................. 435/15 |
| 6,774,221 | B1 | * | 8/2004 | Nishimura et al. .......... 530/402 |
| 2003/0119065 | A1 | * | 6/2003 | Lin et al. ...................... 435/7.1 |

FOREIGN PATENT DOCUMENTS

JP    5-232006    * 9/1993

OTHER PUBLICATIONS

Man et al. "Prediction of the odorant binding site of olfactory receptor proteins by human-mouse comparisons". Protein Science (2004), 13:240-254.*
Schacham et al. "Predict Modeling and In-Silico Screening for G-Protein Coupled Receptors". Proteins: Structure, Function and Bioinformatics (2004) 57:51-86.*
Bowie et al. (1990) Science 247:1306-1310.*
Ngo et al. 1994, in: The Protein Folding Problem and Tertiary Structure, pp. 492-495, Merz et al., Eds., Birkhauser, Boston.*
Reineke et al. "A synthetic mimic of a discontinuous binding site on interleukin-10" Nature Biotechnology vol. 17 (Mar. 1999), p. 271-275.*
Wodak et al. "Prediction of protein-protein interactions: the CAPRI experiment, its evaluation and implications" (2004) Current Opinion in Structural Biology 14:242-249.*
Tcatchoff et al. "A single lysyl residue defines the binding specificity of a human odorant-binding protein for aldehydes" FEBS Letters 580 (2006) 2102-2108.*
Burgess et al. J Cell Bio. 111:2129-2138, 1990.*
Lazar et al. Molecular and Cellular Biology 8:1247-1252 (1988).*
Ferscht et al. Structure and Mechanism in Protein Science (1999), W.H. Freeman and Company, New York, Chapter 1, pp. 4-8.*
Berg et al. Biochemistry (2002), Fifth Edition, W.H. Freeman and Company, New York, pp. 107-113.*
Wu et al. "Synthetic peptide mimicking of binding sites on olfactory receptor protein for use in 'electronic nose'" Journal of Biotechnology 80 (2000) 63-73).*
Molecular Simulations, Inc., Manual for "Affinity: Release 2000" (Mar. 2000), San Diego, CA, Chapter 1, pp. 7-12 and 61, retrieved from http://www.accelrys.com/doc/pdf/affinity2K.pdf.*
Afshar et al. "Towards structural models of molecular recognition in olfactory receptors" Biochimie 1998 Feb;80(2):129-35.*
Parmentier et al. "Expression of members of the putative olfactory receptor gene family in mammalian germ cells" Nature (1992) 355(6359):453-5.*
Wu et al. "A piezoelectric biosensor as an olfactory receptor for odour detection: electronic nose" Biosensors & Bioelectronics 14 (1999) 9-18.*
Konig et al. "Long-term stability and improved reusability of a piezoelectric immunosensor for human erythrocytes" Analytica Chimica Acta, vol. 280, No. 1, 1993, p. 37-41.*
A. Caflisch et al. "Monte Carlo Docking of Oligopeptides to Proteins". Proteins: Structure, Function and Genetics 13:223-230, 1992.
M. E. Clamp et al. "Hybrid Monte Carlo: An Efficient Alogrithm for Condensed Matter Simulation". Journal of Computational Chemistry 15(8):838-846, 1994.
T. N. Hart et al. "A Multiple-Start Monte Carlo Docking Method". Proteins: Structure, Function and Genetics 13:206-222, 1992.
P. Herzyk et al. "Automated Method for Modeling Seven-Helix Transmembrane Receptors from Experimental Data". Biophysical Journal 69:2419-2442, 1995.

(Continued)

*Primary Examiner*—Christopher L Chin
*Assistant Examiner*—Christine Foster
(74) *Attorney, Agent, or Firm*—Occhiuti Rohlicek & Tsao LLP (57) ABSTRACT

A biosensor, a method of making a biosensor, and a method of using a biosensor are described. A biosensor includes a transducer and a peptide encoding the most probable binding domain of an olfactory receptor protein. In embodiments, the transducer is a piezoelectric crystal. The method of making a biosensor includes modeling the three dimensional structure of an olfactory receptor protein; identifying the most probable binding domain of an olfactory receptor protein using a protein docking program; synthesizing a peptide encoding the most probable binding domains or a part thereof; and attaching the peptide to a transducer.

7 Claims, 5 Drawing Sheets

OTHER PUBLICATIONS

E. Katchalski-Katzir et al. "Molecular surface recognition: Determination of geometric fit between proteins and their ligands by correlation techniques". Proc. Natl. Acad. Sci. USA 89:2915-2199, Mar. 1992.

Z. Li et al. "Monte Carlo-minimization approach to the multiple-minima problem in protein folding". Proc. Natl. Acad. Sci. USA 84:661-6615, Oct. 1987.

B. A. Luty et al. "A Molecular Mechanics / Grid Method for Evaluation of Ligand-Receptor Interactions". Journal of Computational Chemistry 16(4):454-464, 1995.

H. Senderowitz et al. "A Smart Monte Carlo Technique for Free Energy Simulations of Multiconformational Molecules: Direct Calculations of the Conformational Populations of Organic Molecules". J. Am. Chem Soc. 117:8211-8219, 1995.

I. A. Vakser. "Protein docking for low-resolution structures". Protein Engineering 3(4):371-377, 1995.

M. Y. Mizutani et al. "Rational Automatic Search Method for Stable Docking Models of Protein and Ligand". J. Mol. Bio. 243:310-326, 1994.

* cited by examiner

| Sequence information | | |
|---|---|---|
| Length: 313 AA | Molecular weight: 35197 Da | CRC64: 2BFFE87F1036EEAA |

```
        10         20         30         40         50         60
         |          |          |          |          |          |
MTEKNQTVVS EFVLEGEPID PQQRDLFYAE FLAMYVTTIL GNLLIIVLIQ LDSHLHTPMY 70         80         90        100        110        120
         |          |          |          |          |          |
LFLSNLSFSD LCFSSVTMPK LLQNMQSQVP SIPYAGCLTQ MYFFLFFGDL ESFLLVAMAY 130        140        150        160        170        180
         |          |          |          |          |          |
DRYVAICFPL HYTTIMSPKL CFSLLVLSWV LTMFHAVLHT LLMARLCFCA NTIPHFFCDM 190        200        210        220        230        240
         |          |          |          |          |          |
SALLKLACSD TQYNELVIFI MGGLILVIPF LLIITSYARI VSSILKVPSA IGICKVFSTC 250        260        270        280        290        300
         |          |          |          |          |          |
GSHLSVVSLF YGTVIGLYLC PSANNSTVKE TIMAMMYTVV TPMLNPFIYS LRNKDMKGAL

310
         |
RRVIGRKKIT FSY
```

METHOD FOR FABRICATING AN OLFACTORY RECEPTOR-BASED BIOSENSOR

CROSS-REFERENCE TO RELATED APPLICATIONS

This application is a continuation-in-part of application Ser. No. 10/262,832, now U.S. Pat. No. 7,186,799 filed Oct. 3, 2002, which claims priority to Taiwan application 90131930, filed Dec. 21, 2001, and application Ser. No. 09/535,814, filed Mar. 28, 2000, now abandoned which is a continuation-in-part of application Ser. No. 09/057,181, filed Apr. 8, 1998, now abandoned, the entire disclosures of each of which are incorporated herein by reference.

BACKGROUND

Chemoreception enables organisms to detect chemicals in its environment. In humans, odor receptor cells are located in the nose. The biochemical receptors for the odorants are transmembrane proteins found in the membrane of receptor cells cilia. Olfactory receptor proteins (ORPs) generally have seven non-intersecting helices.

The detection of environmental chemicals is mediated by peripheral olfactory organs of varied complexity in almost all metazoans. Typically, specialized sensory neurons initiate perception by detecting ambient molecules, commonly called odors, that interact with protein receptors in their membranes. ORPs on the cilia detect the odorants entering the nose. ORPs are coded by approximately 1000 genes, and it is the largest gene family in the genome of any species. ORPs are members of the proteins having seven transmembrane domains, i.e. G-protein couple receptor (GPCR) super-family. They have diverse amino acid sequences and are able to recognize a wide variety of structurally diverse odorants. The amino acid sequences of ORPs are especially variable in the several transmembrane domains. This is a possible mechanism for the recognition of a variety of structurally diverse ligands.

Figure 1:
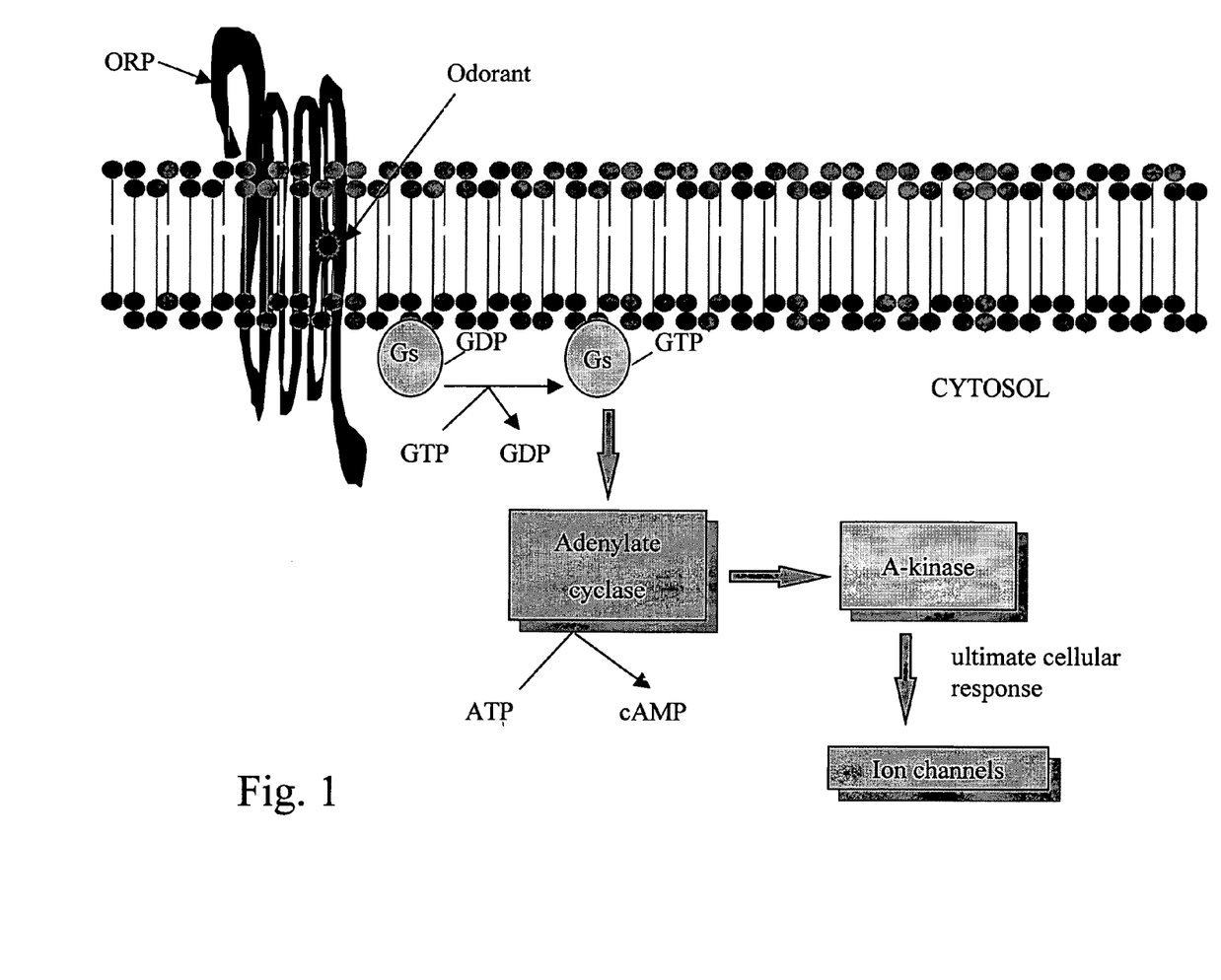
FIG. 1 is a diagram illustrating the major pathway of olfactory transduction.

A major path of olfactory transduction is shown in FIG. 1. Binding of the odor molecules to the receptors may activate a G-protein coupled enzymatic cascade to generate second messengers. These messengers can open the ion channels on the membrane of olfactory cells. The opening of channels may depolarize the membrane and lead to action potentials and signaling.

SUMMARY

In one aspect, the invention features a biosensor comprising a transducer and a peptide, which is a predicted odorant binding domain of an olfactory receptor protein, such as the most probable odorant binding domain. The odorant binding domain can be predicted by a method described herein. The olfactory receptor protein can be, for example, a mammalian protein, such as a human or canine protein. The transducer can be a piezoelectric crystal. The peptide can be coated on the crystal.

In another aspect, the invention features a biosensor comprising a transducer and a peptide capable of detecting an odorant, e.g., an amine.

Embodiments may include one or more of the following. The peptide may detect trimethylamine, dimethylamine, monomethylamine, and ammonia, and/or can discriminate between such compounds. The peptide can include one or more of the following amino acid sequences: Asp-Pro-Asp-Gln-Arg-Asp (SEQ ID NO:1), Asp-Pro-Asp-Gln-Arg-Asp-Cys (SEQ ID NO:4), Gly-Asp-Leu-Glu-Ser-Phe (SEQ ID NO:2), Gly-Asp-Leu-Glu-Ser-Phe-Cys (SEQ ID NO:5), Phe-Phe-Leu-Phe-Phe-Gly-Asp (SEQ ID NO:3) and Cys-Phe-Phe-Leu-Phe-Phe-Gly-Asp (SEQ ID NO:6). The transducer may be a piezoelectric crystal.

In another aspect, the invention features a method of making a biosensor. The steps of the method include modeling the three dimensional structure of an olfactory receptor protein; identifying the most probable binding domain of an olfactory receptor protein using a protein docking program; synthesizing a peptide encoding the most probable binding domains or a part thereof; and attaching the peptide to a transducer.

Embodiments may include one or more of the following. The transducer may be a piezoelectric crystal. The most probable binding domains may include one or more sequences from transmembrane domains 1, 3, or 5 of the olfactory receptor protein.

In another aspect, the invention features a method of detecting an amine molecule with a biosensor containing a crystal transducer. The method consists of contacting the biosensor to a test sample and determining if the frequency of the piezoelectric crystal is altered by presence of the test sample, thereby detecting an amine in the test sample.

"Amine" or "amine compound" herein means a compound having a $NR_3$ group. R is an alkyl group or an aryl group. Examples of $NR_3$ group in the present invention are trimethylamine, dimethylamine, monomethylamine and ammonia groups.

DETAILED DESCRIPTION

Abbreviations:
  Trimethylamine: TMA,
  Dimethylamine: DMA,
  Monomethylamine: MMA, and
  Ammonia: $NH_3$.

Sensors which function like olfactory receptor proteins can be used to detect specific molecules. Sensors can be developed based on a naturally occurring protein, e.g., a seven transmembrane spanning protein or an olfactory receptor protein. One method for developing sensors includes determining the secondary and/or tertiary molecular structures of olfactory receptor proteins having olfactory receptor binding domains specific to selected ligands of interest.

One application of a biosensor is to detect elevated amine levels in the breath. Many disorders, such as kidney disease, uremia, liver disease, and stomach ulcer, are accompanied by elevated amine levels in the breath. The disorder therefore can be diagnosed by determining the amine level in the breath. One way to diagnosis such disorders is to build a database containing results using the sensor on persons without a particular disorder and results using the sensor on person with a particular disorder. When the diagnosis is carried out, the amine content of the patient is measured using the sensor and comparing the results with the results in the database. If the patient results are more similar to the results for persons without the disorder, then the patient is likely to be free of the disorder. If the patient results are more similar to the results for person with the disorder, then the patient is more likely to have the disorder.

Another application of a biosensor is to test the freshness of seafood. Spoiled seafood, such as fish and shellfish, releases amine compounds. Therefore, the freshness of seafood can be tested by measuring the level of amine compounds released using the sensor.

The sample to be tested can be gas, liquid, or solid. For example, the sample can be air, breath, water, seafood, body fluid such as blood or urea of a live subject, or volatile vapor of body fluid of such a subject. Accordingly, another application of biosensor is to test air or water quality by determining amine levels in air or water, respectively.

A method for identifying a putative odorant binding domain of an olfactory receptor protein (ORP) molecules can begin with identification and molecular cloning of genes that code for the receptor protein of interest. These genes are then expressed and the target protein is isolated and purified. Physical studies such as X-ray diffraction, neutron diffraction and electron microscopy are conducted to determine 2-D maps and 3-D structure; site directed mutagenesis is conducted to determine the position of residues for ligand binding. However, it is also possible to identify an odorant binding domain or peptide without actual structure determination.

In one embodiment, selecting which peptide to be included in the sensor is based on the analysis of secondary structure of an olfactory receptor protein, and the simulation of the binding site between the tertiary structure of the olfactory receptor protein and the target odorant molecule. The physical and chemical properties of the substance to be examined is also considered. Together with a sensor such as a biochip, the peptide is used for detecting amine.

The method for detecting a molecule of interest using a bio-sensor comprises the application of a sensor to examine a sample, wherein the sensor is coated with a peptide. The results collected from the sensor are then processed and compared with a database to determine the quantity of a molecule of interest present in a sample.

The apparatus for detecting a molecule of interest comprises a sensory device, a peptide, and a signal processing device coupled to the sensory device, where the peptide coats the sensory device. The amount of a molecule of interest in a sample is determined based on the binding of the molecule of interest with the peptide. The sensor device can be a transducer such as a biochip, piezoelectric quartz crystal, surface acoustic wave, electrochemical sensor, fiber optic, surface plasmon resonance, or metal oxide semiconductor.

A piezoelectric quartz crystal biological sensor is one of the most promising sensors currently in use. A preferred embodiment of the present invention uses a piezoelectric quartz crystal biological sensor. The sensor comprises a piezoelectric quartz crystal and a peptide, where the peptide is coated on the piezoelectric quartz crystal to form a sensor. When the peptide reacts and binds to a molecule of interest, the frequency of the piezoelectric quartz crystal changes due to the change in mass.

In one embodiment of a biochip of an artificial nose, the peptide is used for a receptor and is configured as a coating layer on a transducer. The receptor is preferably a transducer utilizing a piezoelectric quartz crystal. When the receptor and the gas molecule react, a mass change is creating affecting the frequency of the quartz crystal. The magnitude of the reaction is indicated by the change in the frequency of the crystal. The prediction method can also be used to select peptides that have the best sensitivity and affinity to the gas molecules. Furthermore, the quality of the peptides can be controlled by the synthesizing method such that it can be used in artificial nose detection.

EXAMPLES

Without intending to limit in any manner, the present invention will be further illustrated by the following examples using a piezoelectric quartz crystal as the sensor.

Example 1

OLFD CANFA (P30955)

Figure 2:
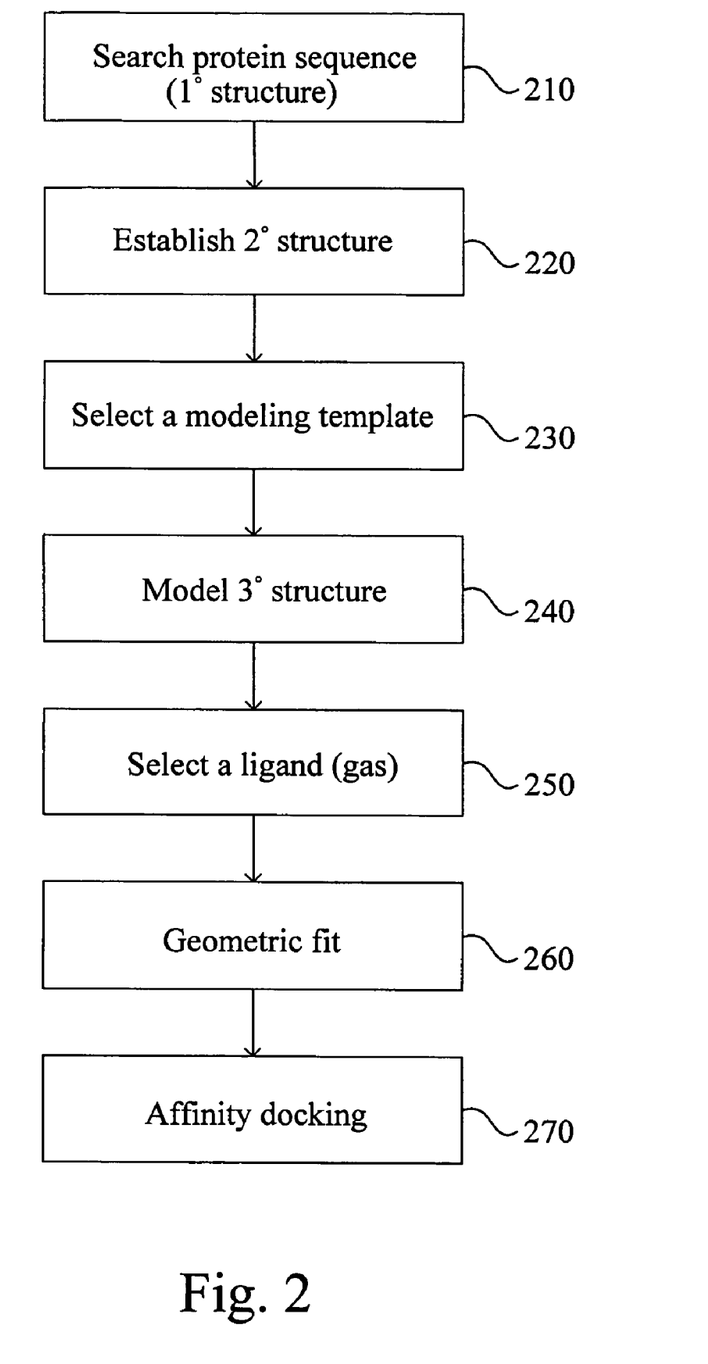
FIG. 2 is a flow chart illustrating the modeling steps of the present invention.

The following example illustrates one method of making a biosensor. FIG. 2 is a flow chart detailing the modeling steps of the preferred embodiment. In step 210 of FIG. 2, an olfactory receptor protein that has been selected is sequenced. It may be sometimes be desirable to actually clone, express, and isolate the selected ORP, but, in most instances, the ORP is chosen from a sequence database based on the ORP's primary amino acid sequence's similarity with other known ORPs. One preferred database for selecting the ORP is the ExPASy server of the Swiss Institute of Bioinformatics. Other similar databases or print sources may be equally suitable.

Figure 3:
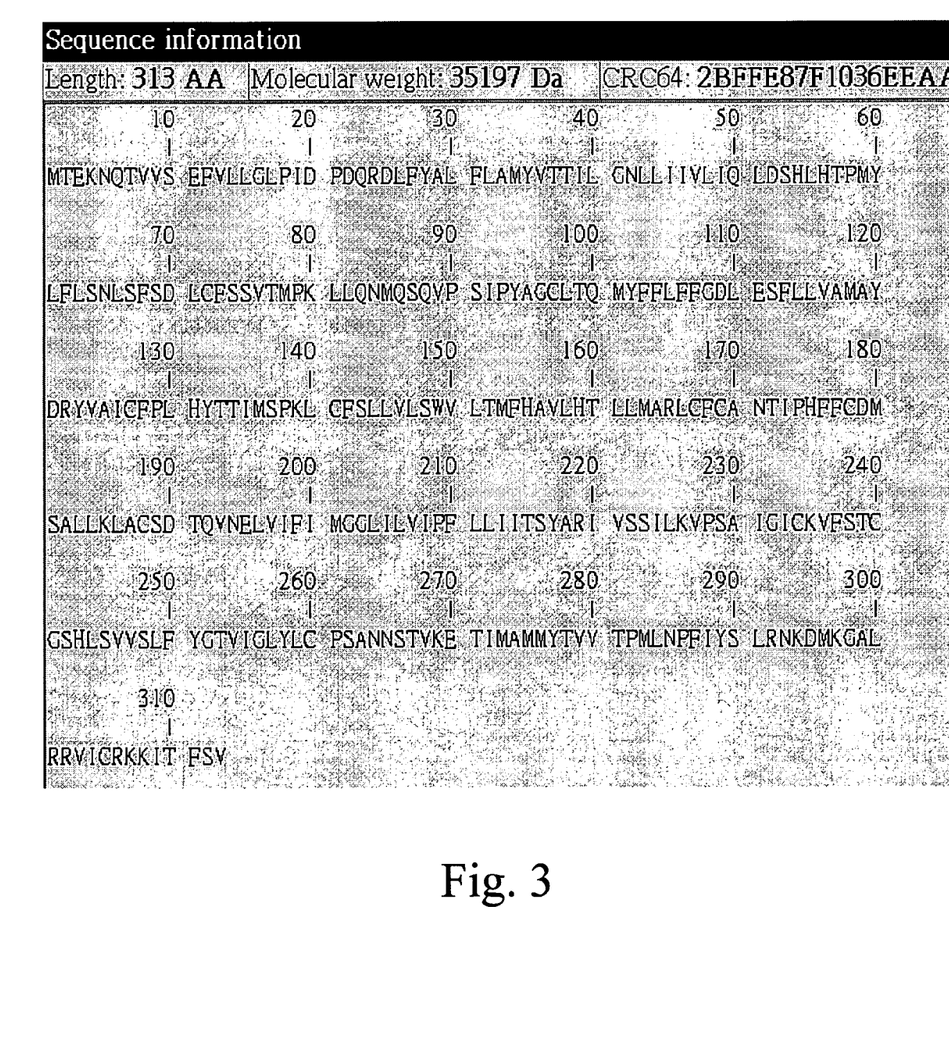
FIG. 3 is an amino acid sequence for OLFD_CANFA (P30955) (SEQ ID NO:15).
Figure 4:
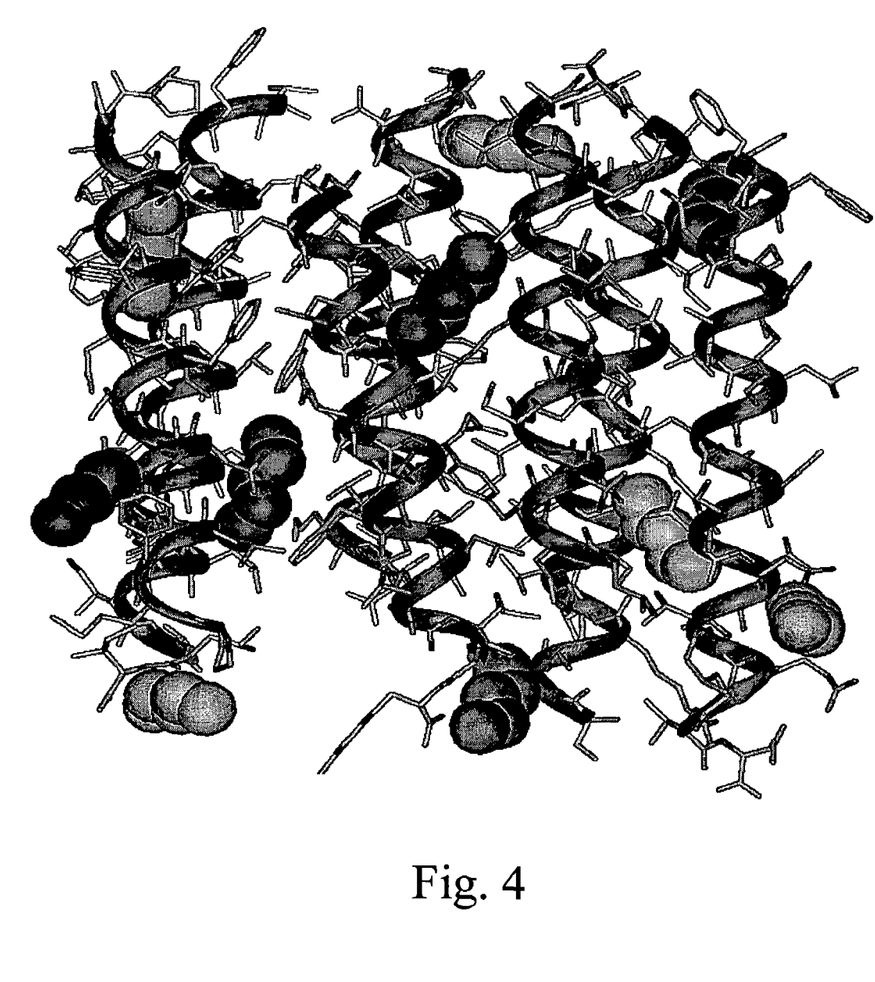
FIG. 4 is a three dimensional structure showing the simulation results of the olfactory receptor protein, OLFD_CANFA (P30955), docking with trimethylamine which is shown as spherical molecular models.
Figure 5:
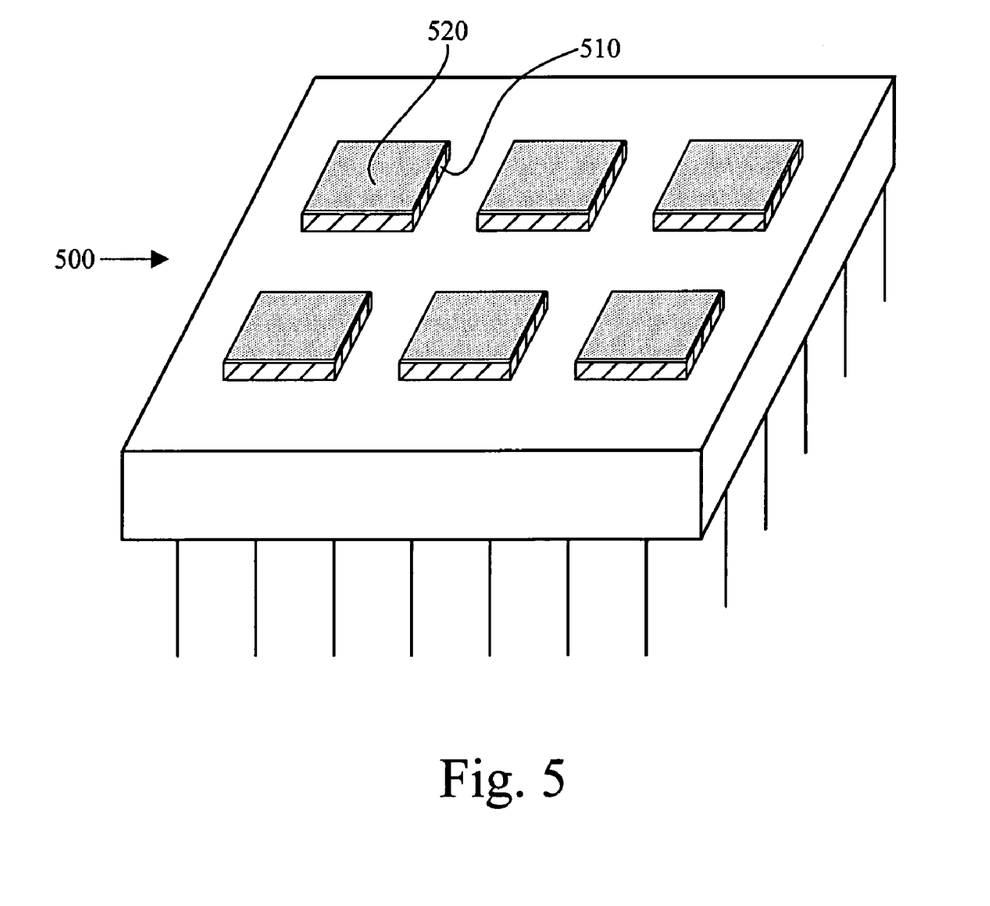
FIG. 5 is a perspective view of a transducer made in accordance with a preferred embodiment of the present invention.

The ExPASy server contains the "SWISS PROT and TrEMBL" database. The ExPASy server is open to the public and may be accessed via the Internet. Using the keyword search features of this server and the key words "olfactory receptor", a subset of sequences of olfactory receptor proteins can be created. From the subset of ORPs, one ORP can be selected. For example, OLFD_CANFA (P30955) is an ORP selected from the "SWISS PROT and TrEMBL" database. The selected ORP sequence comes along with additional information relating to the ORP such as EMBL cross references, length, molecular weight, and amino acid sequence information. The amino acid sequence information is generally subdivided into potential extracellular, transmembrane, and cytoplasmic domains, which are predicted and provided only for reference. The amino acid sequence of OLFD_CANFA (P30955, SEQ ID NO:15) is shown in FIG. 3, and the predicted secondary-structure features of OLFD_CANFA (P30955) are listed in Table 1.

TABLE 1

| Key | Position | Length | Description |
| --- | --- | --- | --- |
| Domain | 1-25 | 25 | Extracellular (potential) |
| Transmem | 26-49 | 24 | 1 (potential) |
| Domain | 50-57 | 8 | Cytoplasmic (potential) |
| Transmem | 58-79 | 22 | 2 (potential) |
| Domain | 80-100 | 21 | Extracellular (potential) |
| Transmem | 101-120 | 20 | 3 (potential) |
| Domain | 121-139 | 19 | Cytoplasmic (potential) |
| Transmem | 140-158 | 19 | 4 (potential) |
| Domain | 159-195 | 37 | Extracellular (potential) |
| Transmem | 196-218 | 23 | 5 (potential) |
| Domain | 219-235 | 17 | Cytoplasmic (potential) |
| Transmem | 236-259 | 24 | 6 (potential) |
| Domain | 260-271 | 12 | Extracellular (potential) |
| Transmem | 272-291 | 20 | 7 (potential) |
| Domain | 292-313 | 22 | Cytoplasmic (potential) |

In step 220 of FIG. 2, the predicted secondary structure, such as α-helices, β-sheets, and transmembrane regions, of the ORP under investigation is determined by using, for example, the "PredictProtein" server of the "BIOcomputing 3D Modeling Unit Service" (B Rost: PHD: predicting one-dimensional protein structure by profile based neural networks. Methods in Enzymology, 266, 525-539,1996). The "PredictProtein" server can be accessed via the internet. "PredictProtein" includes sequence analysis and structure prediction. One can submit any protein sequence, and then "PredictProtein" retrieves similar sequences in the database and predicts aspects of protein structure. The "PredictProtein" server uses several programs, such as those listed in Table 2, to predict protein structure.

TABLE 2

| Program's Type | Program | Function |
|---|---|---|
| Alignment and database searching methods | MaxHom | MaxHom is a dynamic multiple sequence alignment program which finds similar sequence in a database. |
| Sequence motif searching methods | ProSite | ProSite is a database of functional motifs. |
| | ProDom | ProDom is a database of putative protein domains; searched with BLAST for domains corresponding to sequence being investigated. |
| Prediction of protein structure | PHDsec | PHDsec predicts secondary structure from multiple sequence alignments. |
| | PMDacc | PMDacc predicts per residue solvent accessibility from multiple sequence alignments. |
| | PHDhtm | PHDhtm predicts the location and topology of transmembrane helices from multiple sequence alignments. |
| | GLOBE | GLOBE predicts the globularity of a protein. |
| | TOPITS | TOPITS is a prediction-based threading program, that finds remote structural homologues in the DSSP database. |
| | COILS | COILS finds coiled-coil regions in your protein. |
| | EvalSec | EvalSec evaluates secondary structure prediction accuracy. |

In essence, PredictProtein allows sequences of ORPs to be submitted for comparison to the sequences of proteins in the PredictProtein database. PredictProtein retrieves similar sequences and predicts secondary protein structure based on those similar sequences. PredictProtein performs and displays the results of a "PROSITE" motif search, "ProDom" domain search, MAXHOM alignment header analysis, and provides information regarding accuracy of the foregoing analyses. The prediction of secondary structure is performed by PredictProtein using a system of neural networks.

The MAXHOM program produces a multiple sequence alignment file which serves as the input for the neural network system. The output of the MAXHOM analysis includes identification of aligned proteins, percentage of pairwise sequence identity, percentage of weighted similarity, number of residues aligned, number of insertions and deletion (indels), number of residues in all indels, length of aligned sequences, and a short description of the aligned proteins. The preferred neural network for prediction of secondary structure is described in "Prediction of Protein Structure at Better than 70% accuracy" J. Mol. Bio., 1993, 232, 584-599, and the entire disclosure of which is incorporated by reference.

Prediction of solvent accessibility is also determined (PHDacc) in accordance with "The Analysis and Prediction of Solvent Accessibility in Protein Families" Proteins, 1994, 20, 216-226, and the entire disclosure of which is incorporated by reference. The latter prediction provides values for relative solvent accessibility. Prediction of helical transmembrane segments of the ORP is performed by the PHDhtm program. The PHDhtm program predicts the secondary structure (helix, sheet, loop) of the ORP and relative location of the secondary structure to the membrane (inside, outside, transmembrane) with relative accuracy. Preferably, the predicted topology for the transmembrane proteins is determined using PHDtopology and fold recognition is determined by predicted-based threading using PHDthreader. The secondary structure predictive determinations are verified for accuracy using EvalSec. All of the computer programs used in the present invention can be accessed by the public, and their disclosures are incorporated herein by reference.

For example, primary amino acid sequence of OLFD_CANFA (P30955) is inputted into the "PredictProtein" server. Since most of odorant molecules bind to transmembrane helices of an ORP, the predicted seven transmembrane helices of the OLFD_CANFA (P30955) are listed in Table 3.

TABLE 3

| Number of helix | Sequence from SEQ ID NO:15 | Position of amino acids |
|---|---|---|
| 1 (SEQ ID NO:8) | Phe Tyr Ala Leu Phe<br>Leu Ala Met Tyr Val<br>Thr Thr Ile Leu Gly<br>Asn Leu Leu Ile Ile<br>Val Leu Ile Gln | 27-50 |
| 2 (SEQ ID NO:9) | Leu His Thr Pro Met<br>Tyr Leu Phe Leu Ser<br>Asn Leu Ser Phe Ser<br>Asp Leu Cys Phe Ser<br>Ser Val | 55-76 |
| 3 (SEQ ID NO:10) | Leu Thr Gln Met Tyr<br>Phe Phe Leu Phe Phe<br>Gly Asp Leu Glu Ser<br>Phe Leu Leu Val Ala<br>Met Ala Tyr Asp | 98-121 |
| 4 (SEQ ID NO:11) | Cys Phe Ser Leu Leu<br>Val Leu Ser Trp Val<br>Leu Thr Met Phe His<br>Ala Val Leu His Thr<br>Leu Leu Met | 141-163 |
| 5 (SEQ ID NO:12) | Val Ile Phe Ile Met<br>Gly Gly Leu Ile Leu<br>Val Ile Pro Phe Leu<br>Leu Ile Ile Thr Ser<br>Tyr Ala Arg Ile Val | 197-221 |
| 6 (SEQ ID NO:13) | Ser His Leu Ser Val<br>Val Ser Leu Phe Tyr<br>Gly Thr Val Ile Gly<br>Leu Tyr Leu | 242-259 |
| 7 (SEQ ID NO:14) | Met Ala Met Met Tyr<br>Thr Val Val Thr Pro<br>Met Leu Asn Pro Phe<br>Ile Tyr Ser | 273-290 |

In step 230 in FIG. 2, after determining the predicted seven transmembrane helices, a template protein used to predict the approximate tertiary structure of the transmembrane helices is selected. Template selection can be performed using the Swiss-Model interface program and BLAST (Basic local alignment search tool as described in J. Mol. Biol. 215:403-410, the entire disclosure of which is incorporated herein by reference). To begin, the complete sequence of the ORP under investigation is inputted into the Swiss-Model interface, and then the BLAST program determines the most appropriate modeling template to be used in the tertiary structure investigation. The modeling template will be that protein (of known primary, secondary and tertiary structures) having the highest primary sequence homology and similar secondary structure with the ORP being investigated.

For example, the primary amino acid sequence of OLFD_CANFA (P30955) is inputted into the Swiss-Model interface. Since OLFD_CANFA (P30955) has seven transmembrane helices, the primary sequence of OLFD_CANFA (P30955) is compared with the sequences of proteins in the seven transmembrane subset of the SWISS-PROT database by the BLAST program. Then, a number of BLAST-assisted templates, as listed in Table 4, are obtained. In Table 4, Neuropeptide Y1 receptor (P25929) has the largest P(N), i.e. Neuropeptide Y1 receptor (P25929) has the highest primary sequence homology with the OLFD_CANFA (P30955). Therefore, Neuropeptide Y1 receptor (P25929) is selected to be the modeling template for OLFD_CANFA (P30955).

TABLE 4

| SWISS-PROT Code | Seven helices modeling template | P(N) | Smallest Poisson Probability N |
|---|---|---|---|
| P25929 | Neuropeptide Y1 receptor (*Homo sapiens*) | 42 | $6.1 \times 10^{-2}$ |
| P07550 | Beta-2 adrenergic receptor (*Homo sapiens*) | 37 | $2.8 \times 10^{-1}$ |
| P21452 | Substance-K receptor (Neurokinin A receptor) | 39 | $7.0 \times 10^{-4}$ |
| P02699 | Rhodopsin (*Bos Taurus*) | 41 | $5.1 \times 10^{-8}$ |
| P02945 | Bacteriorhodopsin (*Halobacterium halobium*) | *NA | *NA |

*NA: not available.

After the modeling template has been selected, the sequences of the helical regions are displayed and the sequences of the helices of the ORP under investigation (as determined in the secondary structure analysis step) are inputted into the Swiss-Model interface program in step 240. In other words, the helical regions of the template are aligned with the helical regions of the ORP under investigation. The comparison yields a predicted tertiary structure of the ORP being investigated on an atom-by-atom basis. The predicted tertiary structure of the ORP being investigated is preferably outputted as a file containing three coordinates for each atom in the ORP. For example, a lengthy list of three coordinates of each atom in OLFD_CANFA (P30955) was obtained.

The preferred protocol for the step 240 includes energy minimization and the like as described in: ProMod and Swiss-Model: Internet-based Tools for Automated Comparative Protein Modeling, Biochem. Soc. Trans. V. 24 274 1996; Large-Scale Comparative Protein Modeling, Proteome Research: New Frontiers in Functional Genomics 177 1997; Swiss-Model and the Swiss-PDBviewer; an Environment for Comparative Protein Modeling, Electrophoresis, V. 18 2714 1997; Automated Modeling of the Transmembrane Region of G-Protein Coupled Receptor by Swiss-Model, Receptors; and Channels v. 4 161 1996; Protein Modeling by email, Bio/Technology V. 13 658 1995, the disclosures of which are incorporated by reference.

The modeling software programs used in this example have a high degree of sophistication. For example, ProMod, which is under SWISS-MODEL Repository of the ExPASy Molecular Biology Server, applies a Protein Modeling tool which requires similarities with experimentally determined protein structures. It is a knowledge-based approach to predictive structure determination. It requires at least one known 3D structure of a related protein and good quality sequence alignments, where the degree of sequence identity affects the accuracy of the predictive structure.

In ProMod, there is a superposition of related 3D structures. A multiple alignment with the sequence under investigation is made. A framework for the new sequence is made and any missing loops are rebuilt. The backbone of the structure is completed and corrected if required. Side chains are corrected and rebuilt. The resultant structure is verified and packing is checked. The structure is then refined by energy minimization and molecular dynamics considerations.

The tertiary structures of the helices of the ORP under investigation are thus determined in step 240 and may be viewed stereoscopically using a program such as Insight II, a commercial program provided by Molecule Simulations Inc. and now provided by Accelrys Inc.; Swiss PDB-viewer; or the like.

Next, in step 250, a ligand is selected. A number of assays may be used to determine which ligands have high general binding affinities for the ORP under investigation. The molecular structure of the ligand and the ORP under investigation is then inputted into the Insight II program, i.e. the tertiary structures of ORP helices and the ligand are inputted.

Next, in step 260, the most probable geometrical binding domains of the ORP under investigation and the ligand are determined, preferably using the Global Range Molecular Modeling program (GRAMM), by geometric recognition algorithms. As understood by those skilled in the art, GRAMM is a program for protein docking and it treats the ORP and the ligand as rigid bodies. Since GRAMM utilizes geometric recognition algorithms to determine the most probable geometrical binding domains of a protein for a ligand, no specific information about the binding sites is required. It performs a six-dimensional search through the relative translations and rotations of the molecules. It takes an empirical approach to smoothing the intermolecular energy function by changing the range of atom-atom potentials. It allows the user to locate the area of the global minimum of intermolecular energy for structures of different accuracy.

Then, in step 270, the structures of the ORP and the ligand are allowed to relax. The structures of the ORP and the ligand are flexible. Bond stretching, valence angle bending, torsion, van der Waals force, and electrostatic force of both the ORP and the ligand are taken into consideration. The Affinity Docking program, an embedded program of Insight II, can be used to calculate the energy distribution and reaction forces between the ligand and the geometrical binding domains, as predicted by GRAMM, of the ORP by molecular mechanics calculations using the energy minimization algorithm. AFFINITY can include a suite of programs for automatically docking a ligand to a receptor. AFFINITY can automatically find optimal binding structures using an energy-driven classification, e.g., as described by Kuntz et al. (Acc. Chem. Res. 1994, V. 27, p.117). AFFINITY includes two commands which use a Mote Carlo type procedure to dock a guest molecule to a host. The bulk of the receptor, defined as atoms not in the binding site specified, is held rigid during the docking process while the binding site atoms and ligand atoms are moveable. But the commands differ in their treatment of non-bond interactions. In GRIDDOCKING, interactions between bulk and movable atoms are approximated by the molecule mechanical/grid (MM/Grid) method developed by Luty et al. (Journal of Computational Chemistry, 1995, V. 16, pp. 454-464). FixedDocking computes non-bond interactions using cutoff methods and cell multiple method and it does not include solvation terms.

Catflisch et al. (Proteins: Structure, Function, and Genetics, 1992, V. 13, pp.223-230) developed a two step procedure for docking flexible ligands. Their procedure is to first dock the ligand using a special energy function designed to remove bad contact between the ligand and the receptor efficiently. Then Monte Carlo minimization (Li and Scheraga, Proc. Natl. Acad. Sci. 1987, V. 84, pp.6611-6615) is carried out to refine the docked structures using molecular mechanics. Hart and Read (Proteins: Structure, Function, and Genetics 1992, V. 13, pp. 206-222) also employ to steps to dock ligands. They use a score function based on receptor geometry to approximately dock ligands in the first step, and then use Monte Carlo minimization similar to that of Catflisch et al (Proteins: Structure, Function, and Genetics, 1992, V.13, pp.223-230) for the second step. The method by Mizutani et al (J. Mol. Biol., 1994, V. 243, pp.310-326) is another variation of this two step method.

AFFINITY is quite similar to the above two-step methods. It also uses a Monte Carlo procedure in docking ligands, but there are a few important distinctions. First, the Monte Carlo procedure in Affinity can be used in conjunction either with energy minimization (to mimic the Monte Carlo minimization method of Li and Scheraga, Proc. Natl. Acad. Sci. 1987, V. 84, pp.6611-6615) or with molecular dynamics (to mimic the hybrid Monte Carlo method, Clamp et al, Journal of computational chemistry 1994, V.15, pp. 838-846, or the Smart Monte Carlo method, Senderowitz et al, J. Am. Chem. Soc. 1995, V. 117, pp. 8211-8219). This flexibility enables one to apply AFFINITY to a variety of docking problems. Second, in the initial screening of docked structures, AFFINITY employs energy differences obtained from molecular mechanics, while the methods discussed above use empirical rules or descriptors (the first step in their methods). Thus, AFFINITY is more consistent in that it uses molecular mechanics in both initial screening and final refinement of docked structures. Third, AFFINITY allows the binding site of the receptor to relax, while the methods discussed above fix the entire receptor. Fourth, AFFINITY employs two new non-bond techniques which are both accurate and efficient to make docking practical. One is the Grid/MM method of Luty et al (Luty et al Journal of Computational Chemistry, 1995, V. 16, pp. 454-464) which represents the bulk of protein by grids. This method is 10-20 times faster than the no-cutoff method with almost no loss in accuracy. It also incorporates the solvation method of Stouten et al (Molecular Simulation, 1993, V. 10, p.97). The other is the cell multiple method. This method is about 50% slower than the Grid/MM method, but it does not require grid setup. Thus, a typical docking calculation takes about 1-3 hours of CPU time on an Indigo R4400 workstation.

In use, the initial molecule model, after the gas molecule is combined with the ORP, is generated using the GRAMM program. The INSIGHT II-building is then used to identify a suitable force field between the ORP and the gas molecule. The INSIGHT II-discoverer is then used to simulate the atomic interactions between the ORP and the gas molecules. Finally, the Monte Carlo method is added to produce several sets of possible reaction sites between the ORP and the gas molecule. During the modeling with INSIGHT II, the molecule mechanics between the ORP and the gas molecule are used to calculate bond stretching, valence angle bending, torsion, Van der Waals forces, and electrostatics forces. Several local minimization points on the 20 attachment energy distribution can also be generated to indicate the degree of affinity between the attachment of the ORP and the gas molecule. When these factors are properly considered, the most stable attachment structure between the gas molecule and the ORP is determined.

The most probable binding domains are thus determined, and the user can read out the sequence of the binding domains by moving the mouse to each amino acid of the binding domains.

For example, the highly probable binding domains, as shown in FIG. 4, of OLFD_CANFA (P30955) for trimethylamine are predicted. The trimethylamine molecules are shown as spherical molecular models, and OLFD_CANFA (P30955) is shown in cartoon structure. The eight highly probable binding domains of OLFD_CANFA (P30955) for the trimethylamine are located in transmembrane 1, transmembrane 3, and transmembrane 5.

The peptides of the ORP having a useful cross-linking property (e.g., a cysteine) are designed with the gas molecule based upon the position of the peptide having the gas molecule and the ORP reaction in the three-dimensional space. The peptide is then artificially synthesized and used to make the receptor for the artificial nose. Once the three-dimensional structure of the ORP is established and the reaction sites between the gas molecule and the ORP are identified, various peptides associated with the attachment of the ORP to the desired gas molecule are identified and used as a covering substance for biochip receptor of an artificial nose.

For example, peptides are then synthesized corresponding to these highly probable binding domains using conventional synthesis technologies. The peptides are then applied to the surface of a transducer, preferably one fabricated using thin film (semiconductor) technique known to those skilled in the art. Briefly, with reference to FIG. 5, transducers 510 coated with peptide layer 520 are on biosensor 500. Transducer 510 is preferably a piezoelectric quartz crystal-based device. A change will occur if a ligand binds to the peptide layer resulting in a measurable frequency change in the quartz crystal frequency, allowing for the detection of ligand binding. The success and efficiency of the transducer can be determined, including by comparing the sensor's response to the ligand and other molecules. The biochip receptor of artificial nose may then be used to identify various gas molecules associated with smells by monitoring the attachment of the gas molecules to the peptides making up the receptor of the biochip.

For example, peptides synthesized according to the most probable binding domains of OLFD_CANFA (P30955) for trimethylamine are peptides B1, B2, and B3. The amino acid sequences of the peptides B1, B2, and B3 are Asp-Pro-Asp-Gln-Arg-Asp (SEQ ID NO:1), Gly-Asp-Leu-Glu-Ser-Phe (SEQ ID NO:2), and Phe-Phe-Leu-Phe-Phe-Gly-Asp (SEQ ID NO:3). One or more modifying groups can be added to the C— and/or N-terminals of the peptide if desired. The modifying group can be an amino acid or other functional group. Examples of amino acid that can be added include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, preferably a cysteine. Examples for functional group include —COOH, $—NH_2$, —CHO, —OH, or —SH group, wherein —SH group is more preferred. The transducers of a biosensor have gold electrodes; the —SH functional group of the cysteine can react with gold electrodes directly in an organic solution to form a chemical bond between them.

One way to attach these peptides is by dipping the surface of gold electrode on piezoelectric quartz crystal with the peptide solution under room temperature for a period of time.

Then, after attaching these peptides on the transducers of a biosensor, the biosensor is used to detect various gases such as trimethylamine, dimethylamine, monomethylamine, ammonia, acetone, formic acid, ethanol, and formaldehyde. The experimental results of the peptides B1, B2, B3, and Pb2 are listed in Table 6, where the peptide Pb2 is a control and not designed according to the most probable binding domains of OLFD_CANFA (P30955).

TABLE 6

| Gas detected | Frequency changes (Hz) | | | |
|---|---|---|---|---|
| | B1 | B2 | B3 | Pb2 |
| Trimethylamine (5.86 ppm) | 5696 | 488 | 687 | 221 |
| Dimethylamine (3.78 ppm) | 3851 | 578 | 721 | 589 |
| Monomethylamine (4.47) | 3011 | 387 | 394 | 595 |
| Ammonia (4.86 ppm) | 1022 | 206 | 209 | 345 |
| Acetone (7.21 ppm) | 13 | 9 | 9 | 31 |
| Formic acid (1.33 ppm) | 161 | 56 | 85 | 97 |
| Ethanol (4.68 ppm) | -5 | 6 | -5 | 16 |
| Formaldehyde (6.54 ppm) | -25 | -22 | -27 | 19 |

Peptide B1: Asp-Pro-Asp-Gln-Arg-Asp-Cys (SEQ ID NO:4)
Peptide B2: Gly-Asp-Leu-Glu-Ser-Phe-Cys (SEQ ID NO:5)
Peptide B3: Cys-Phe-Phe-Leu-Phe-Phe-Gly-Asp (SEQ ID NO:6)
Peptide Pb2: Leu-Phe-Leu-Ser-Asn-Leu-Ser-Phe-Ser-Asp-Leu-Cys-Ala (SEQ ID NO:7)

In Table 6, the numbers shown in each column under each peptide are frequency changes of the quartz crystal vibration frequency. When the absolute value of the frequency change is larger, the sensitivity for the gas detected is larger. For trimethylamine, all peptides, B1, B2, and B3, show a much more sensitive response than the peptide, Pb2, the control.

Example 2

SEQ ID NO:1

Design of the peptide: the tertiary structure of an olfactory receptor protein was used as a template in the computer program "Insight II" to simulate possible binding sites for amine compounds. The selected peptide sequence was then modified according to properties of different amino acids to obtain a peptide sequence that is both specific and sensitive in binding amine. The modified peptide was immobilized on the transducer as a receptor film. The transducer used in the embodiments was a 12 MHz piezoelectric quartz crystal, on which the peptide is coated. A sensory apparatus was used in determining types and quantity of compounds containing amine groups in a sample.

An amine examining apparatus according to the present invention is formed by coating the peptide of SEQ ID NO:1 to a piezoelectric quartz crystal according to the following procedure.

A peptide can be synthesized by conventional peptide synthesis techniques such as solid phase synthesis, liquid peptide synthesis, enzymatic synthesis, or recombinant DNA technology. SEQ ID NO:1 was synthesized by solid phase synthesis using Wang resin and F-moc as the protecting group in a Peptide Synthesizer (Apply Biosystems, 432A Peptide Synthesizer, USA).

A cysteine was attached to the C— or N-terminal of SEQ ID NO:1. The peptide was then dissolved and diluted in a suitable organic solvent. A 12 MHz piezoelectric quartz crystal with a gold electrode was used. Two to four mL of the peptide solution was applied to the gold electrode for 4 hours in order to immobilize the peptide on the gold electrode. The cysteine at the terminal of the peptide has a —SH group where the sulfur atom forms a steady covalent bond with the gold molecules of the electrode. The apparatus was ready for use when the detected frequency decrement was between 15000 and 20000 Hz. The procedure for coating the peptide on the sensory device can be adjusted according to different properties of the peptide.

The sensory apparatus was tested using volatile vapor of trimethylamine, dimethylamine, monomethylamine, ammonia, acetone, formic acid, ethanol and formaldehyde prepared according to following.

Reagent grade trimethylamine, dimethylamine, monomethylamine, ammonia, acetone, formic acid, ethanol and formaldehyde were separately dissolved in 5 mL of volatile organic solvent. The solution was sealed in separate 120 mL containers for 5 days allowing the space above the solution to reach the saturated vapor pressure. The concentration of the saturated vapor was calculated from the concentration of the solution and the saturated vapor pressure. The saturated vapor was used for the analysis with or without dilution.

The results were analyzed by an analysis system (Smart Biotechnology Co., Ltd., Taipei, Taiwan). About 5 mg/L of volatile vapor was used per test. The specificity and sensitivity of the sensory apparatus towards each of the previously mentioned volatile vapors were tested.

According to Sauerbrey equation (Sauerbrey, Z. Physical, 1959, V. 155 p.206-210), frequency decrement of a piezoelectric quartz crystal is proportional to the mass applied to the piezoelectric quartz crystal. Therefore the coating quantity of peptide is indicated by the frequency decrement (Hz) after the peptide is coated on the piezoelectric quartz crystal. For this example, the coating quantity of SEQ ID NO:1 peptide was 2194 Hz. The frequency decrement when SEQ ID NO:1 peptide reacted with volatile vapor of trimethylamine, dimethylamine, ammonia, acetone, formic acid, ethanol and formaldehyde was shown in Table 6. Table 6 shows that SEQ ID NO:1 peptide bound to trimethylamine, dimethylamine, monomethylamine, and ammonia particularly well, while it bound to other chemicals at very low rates. The results indicate that SEQ ID NO:1 peptide has high specificity and sensitivity in binding with trimethylamine, dimethylamine, monomethylamine, and ammonia. Therefore SEQ ID NO:1 peptide is a suitable for detecting compounds containing amine groups.

Example 3

SEQ ID NO:2

An amine examining apparatus according to the present invention is formed by coating the peptide of SEQ ID NO:2 to a piezoelectric quartz crystal according to the procedure described in Example 2. The amine examining apparatus was tested with volatile vapor of trimethylamine, dimethylamine, ammonia, acetone, formic acid, ethanol and formaldehyde prepared according to the preparation method described in Example 2 and the results were analyzed by an analysis system (Smart Biotechnology Co., Ltd., Taipei, Taiwan). About 5 mg/L of volatile vapor was used in per test. The specificity and sensitivity of the amine examining apparatus towards each of the previously mentioned volatile vapor were tested.

For this example, coating quantity of SEQ ID NO:2 peptide was 283 Hz. The frequency decrement when SEQ ID NO:2 peptide reacted with volatile vapor of trimethylamine, dimethylamine, monomethylamine, ammonia, acetone, formic acid, ethanol and formaldehyde was shown in Table 6. Table 6 shows that SEQ ID NO:2 peptide bound to trimethylamine, dimethylamine, monomethylamine, and ammonia particularly well, while it bound to other chemicals at very low rates. The results indicate that SEQ ID NO:2 peptide has high specificity and sensitivity in binding with trimethylamine, dimethylamine, monomethylamine, and ammonia. Therefore SEQ ID NO:2 peptide is a very suitable tool in detecting compounds containing amine groups.

Finally, while the invention has been described by way of example and in terms of the preferred embodiment, it is to be understood that the invention is not limited to the disclosed embodiments. On the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method of making a biosensor, comprising:
   synthesizing a peptide consisting of the amino acid sequence of SEQ ID NO:1 or SEQ ID NO:2 and optionally an additional amino acid at either the N- or C-terminus of SEQ ID NO:1 or SEQ ID NO:2, and
   attaching the peptide to a transducer to produce a biosensor.

2. The method of claim 1, wherein the transducer is piezoelectric crystal.

3. The method of claim 1, wherein the peptide includes a functional group at its N-terminus, C-terminus, or both, the functional group being selected from the group consisting of —COOH, —NH$_2$, —CHO, —OH, and —SH.

4. The method of claim 3, wherein the functional group is —SH.

5. The method of claim 1, wherein the peptide consists of the amino acid sequence of SEQ ID NO:4 or SEQ ID NO:5.

6. The method of claim 5, wherein the transducer is piezoelectric crystal.

7. The method of claim 1, wherein the peptide consists of the amino acid sequence of SEQ ID NO:1 or SEQ ID NO:2.

* * * * *

```
                        SEQUENCE LISTING

<160> NUMBER OF SEQ ID NOS: 15

<210> SEQ ID NO 1
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 1

Asp Pro Asp Gln Arg Asp
 1               5

<210> SEQ ID NO 2
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 2

Gly Asp Leu Glu Ser Phe
 1               5

<210> SEQ ID NO 3
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 3

Phe Phe Leu Phe Phe Gly Asp
 1               5

<210> SEQ ID NO 4
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 4

Asp Pro Asp Gln Arg Asp Cys
 1               5

<210> SEQ ID NO 5
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 5

Gly Asp Leu Glu Ser Phe Cys
```

<210> SEQ ID NO 6
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 6

Cys Phe Phe Leu Phe Phe Gly Asp
 1               5

<210> SEQ ID NO 7
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 7

Leu Phe Leu Ser Asn Leu Ser Phe Ser Asp Leu Cys Ala
 1               5                  10

<210> SEQ ID NO 8
<211> LENGTH: 24
<212> TYPE: PRT
<213> ORGANISM: Canis familiaris

<400> SEQUENCE: 8

Phe Tyr Ala Leu Phe Leu Ala Met Tyr Val Thr Thr Ile Leu Gly Asn
 1               5                  10                  15

Leu Leu Ile Ile Val Leu Ile Gln
             20

<210> SEQ ID NO 9
<211> LENGTH: 22
<212> TYPE: PRT
<213> ORGANISM: Canis familiaris

<400> SEQUENCE: 9

Leu His Thr Pro Met Tyr Leu Phe Leu Ser Asn Leu Ser Phe Ser Asp
 1               5                  10                  15

Leu Cys Phe Ser Ser Val
             20

<210> SEQ ID NO 10
<211> LENGTH: 24
<212> TYPE: PRT
<213> ORGANISM: Canis familiaris

<400> SEQUENCE: 10

Leu Thr Gln Met Tyr Phe Phe Leu Phe Phe Gly Asp Leu Glu Ser Phe
 1               5                  10                  15

Leu Leu Val Ala Met Ala Tyr Asp
             20

<210> SEQ ID NO 11
<211> LENGTH: 23
<212> TYPE: PRT
<213> ORGANISM: Canis familiaris

<400> SEQUENCE: 11

Cys Phe Ser Leu Leu Val Leu Ser Trp Val Leu Thr Met Phe His Ala

```
                1               5                  10                 15
Val Leu His Thr Leu Leu Met
            20

<210> SEQ ID NO 12
<211> LENGTH: 25
<212> TYPE: PRT
<213> ORGANISM: Canis familiaris

<400> SEQUENCE: 12

Val Ile Phe Ile Met Gly Gly Leu Ile Leu Val Ile Pro Phe Leu Leu
 1               5                  10                 15

Ile Ile Thr Ser Tyr Ala Arg Ile Val
            20                  25

<210> SEQ ID NO 13
<211> LENGTH: 18
<212> TYPE: PRT
<213> ORGANISM: Canis familiaris

<400> SEQUENCE: 13

Ser His Leu Ser Val Val Ser Leu Phe Tyr Gly Thr Val Ile Gly Leu
 1               5                  10                 15

Tyr Leu

<210> SEQ ID NO 14
<211> LENGTH: 18
<212> TYPE: PRT
<213> ORGANISM: Canis familiaris

<400> SEQUENCE: 14

Met Ala Met Met Tyr Thr Val Val Thr Pro Met Leu Asn Pro Phe Ile
 1               5                  10                 15

Tyr Ser

<210> SEQ ID NO 15
<211> LENGTH: 313
<212> TYPE: PRT
<213> ORGANISM: Canis familiaris

<400> SEQUENCE: 15

Met Thr Glu Lys Asn Gln Thr Val Val Ser Glu Phe Val Leu Leu Gly
 1               5                  10                 15

Leu Pro Ile Asp Pro Asp Gln Arg Asp Leu Phe Tyr Ala Leu Phe Leu
            20                  25                  30

Ala Met Tyr Val Thr Thr Ile Leu Gly Asn Leu Leu Ile Ile Val Leu
        35                  40                  45

Ile Gln Leu Asp Ser His Leu His Thr Pro Met Tyr Leu Phe Leu Ser
    50                  55                  60

Asn Leu Ser Phe Ser Asp Leu Cys Phe Ser Ser Val Thr Met Pro Lys
65                  70                  75                  80

Leu Leu Gln Asn Met Gln Ser Gln Val Pro Ser Ile Pro Tyr Ala Gly
                85                  90                  95

Cys Leu Thr Gln Met Tyr Phe Phe Leu Phe Phe Gly Asp Leu Glu Ser
            100                 105                 110

Phe Leu Leu Val Ala Met Ala Tyr Asp Arg Tyr Val Ala Ile Cys Phe
        115                 120                 125

Pro Leu His Tyr Thr Thr Ile Met Ser Pro Lys Leu Cys Phe Ser Leu
    130                 135                 140
```

-continued

```
Leu Val Leu Ser Trp Val Leu Thr Met Phe His Ala Val Leu His Thr
145                 150                 155                 160

Leu Leu Met Ala Arg Leu Cys Phe Cys Ala Asn Thr Ile Pro His Phe
            165                 170                 175

Phe Cys Asp Met Ser Ala Leu Leu Lys Leu Ala Cys Ser Asp Thr Gln
            180                 185                 190

Val Asn Glu Leu Val Ile Phe Ile Met Gly Gly Leu Ile Leu Val Ile
        195                 200                 205

Pro Phe Leu Leu Ile Ile Thr Ser Tyr Ala Arg Ile Val Ser Ser Ile
        210                 215                 220

Leu Lys Val Pro Ser Ala Ile Gly Ile Cys Lys Val Phe Ser Thr Cys
225             230                 235                 240

Gly Ser His Leu Ser Val Val Ser Leu Phe Tyr Gly Thr Val Ile Gly
            245                 250                 255

Leu Tyr Leu Cys Pro Ser Ala Asn Asn Ser Thr Val Lys Glu Thr Ile
            260                 265                 270

Met Ala Met Met Tyr Thr Val Val Thr Pro Met Leu Asn Pro Phe Ile
            275                 280                 285

Tyr Ser Leu Arg Asn Lys Asp Met Lys Gly Ala Leu Arg Arg Val Ile
        290             295                 300

Cys Arg Lys Lys Ile Thr Phe Ser Val
305                 310
```